United States Patent [19]

Saukaitis

[11] Patent Number: 5,986,140
[45] Date of Patent: Nov. 16, 1999

[54] 7,8-DIFLUORO-2,3-DIHYDRO-3-METHYL-4H-1,4-BENZOXAZINE

[75] Inventor: John C. Saukaitis, Corpus Christi, Tex.

[73] Assignee: Clariant Finance (BVI) Limited, Tortola, Virgin Islands (Br.)

[21] Appl. No.: 08/820,743

[22] Filed: Mar. 19, 1997

Related U.S. Application Data

[62] Division of application No. 08/473,619, Jun. 7, 1995, Pat. No. 5,644,056.

[51] Int. Cl.$^6$ .................................................. C07C 215/68
[52] U.S. Cl. .............................................................. 564/442
[58] Field of Search ............................................. 564/442

[56] References Cited

U.S. PATENT DOCUMENTS

| | | | |
|---|---|---|---|
| 2,298,284 | 10/1942 | Emerson | 260/577 |
| 4,382,892 | 5/1983 | Hayakawa et al. | 260/243.3 |
| 4,762,831 | 8/1988 | Grohe et al. | 514/230 |
| 4,859,773 | 8/1989 | Grohe et al. | 544/101 |
| 4,958,045 | 9/1990 | Grohe et al. | 560/20 |
| 5,136,059 | 8/1992 | Fujiwara et al. | 549/427 |

FOREIGN PATENT DOCUMENTS

| | | |
|---|---|---|
| 0 047 005 | 10/1982 | European Pat. Off. . |
| 0 322 815 | 5/1989 | European Pat. Off. . |
| 35 22 406 | 2/1987 | Germany . |

OTHER PUBLICATIONS

Emerson et al., The Reductive Alkylation of Aniline, Journal Amer. Chem. Soc. pp. 2023–2025, 1938.

Emerson et al., The Reductive Alkylation of Aromatic Primary Amines II Journal Amer. Chem. Soc. pp. 3145–3148, 1938.

Hayakawa et al., Synthesis and Antibacterial Activities of Substituted 7–Ox0–2,3–dihydro–7H–pyrido[1,2,3–de] [1,4] benzoxazine–6–carboxylic Acids: pp. 4907–4913—Chem. Pharm. Bull., 1984.

Tanaka et al., Synthetics of Antimicrobial Agents. VII. Synthesis and Antibacterial Activities of Furo [2,3–g]quinoline Derivatives: pp. 4923–4928, Chem. Pharm. Bull. 32, 1984.

Egawa et al., A New Synthesis of 7–H–Pyrido [1,2,3–de] [1,4] benzoxazine Derivatives Including an Antibacterial Agent, Ofloxacin, pp. 4098–4102: Chem. Pharm. Bull. 32, 1986.

Katrizky et al., N–Alkylation of Hindered Secondary Aromatic Amines With 2–Iodobutane: pp. 399–402, Organic Preparation and Procedures Int., 23 (4) 1991.

Radl et al., Structural Modification and New Methods For Preparation 'Of Ofloxacin Analogs: pp. 1937–1943, Collect. Czech. Chem. Commun. (vol. 56) 1991.

*Primary Examiner*—Richard L. Raymond
*Attorney, Agent, or Firm*—Scott E. Hanf

[57] ABSTRACT

7,8-difluoro-2,3-dihydro-3-methyl-4H-1,4-benzoxazine.

1 Claim, No Drawings

7,8-DIFLUORO-2,3-DIHYDRO-3-METHYL-4H-1,4-BENZOXAZINE

This is a division of application Ser. No. 08/473,619 filed Jun. 7, 1995, now U.S. Pat. No. 5,644,056.

BACKGROUND OF THE INVENTION

1. Technical Field

The invention relates to a new method for the preparation of the pyridobenzoxazine, 7,8-difluoro-2,3-dihydro-3-methyl-4H-1,4-benzoxazine.

1. Background

The pyridobenzoxazine, 7,8-difluoro-2,3-dihydro-3-methyl-4H-1,4-benzoxazine is a key intermediate in the synthesis of the fluoroquinolone antibiotic, Ofloxacin which was discovered by I. Hayakawa and Y. Tanaka, Daiichi Seiyaku Co., Ltd., U.S. Pat. No. 4,382,892, 1983. Ofloxacin is one of the leading antibacterial fluoroquinolones in the market today; e.g. see: *Chem.Pharm.Bull.*32 (12) 4907–4913, 4923 (1984); *Daiichi Seiyaku Drugs Future* 1983, 8, 395; *Collect. Czech. Chem. Commun.* (vol. 56), 1937, (1991). The s-(−) isomer of 7,8-difluoro-2,3-dihydro-3-methyl-4H-1,4-benzoxazine can be utilized in the synthesis of the optically active form of Ofloxacin known as Levofloxacin. Levofloxacin is 8 to 128 times more active than Ofloxacin depending upon the bacteria tested, *J. Med. Chem.* 1987, 30, 2283–2286, *Drugs of the Future* 1992, 17(7); 559–563. *Une, T.; Antimicrob. Agents Chemother.* 32; 1336–1340 (1989).

Hayakawa's method of preparation of Ofloxacin is described in EP 0047005A1 and starts with 2,3,4-trifluoronitrobenzene which is converted to the 2-hydroxy-3,4-difluoronitrobenzene in dimethylsulfoxide in the presence of potassium hydroxide. The yield for this reaction is only 29%. The low yield of this step limits the overall yield of Hayaklawa's process. Other patents cite the use of this material in their routes to Ofloxacin; e.g. U.S. Pat. No. 5,136,059 and EP 0333815 A2. The 2-hydroxy-3,4 difluoronitrobenzene is converted to 2-acetonyloxy-3,4-difluoronitro-benzene which is reductively ring closed to give an isomeric mixture of 7,8-difluoro-2,3-dihydro-3-methyl-4H-1,4-berizoxazine (Formula 1). This material is converted to diethyl-(7,8-difluoro-2,3-dihydro-3-methyl 4H 1,4 benzoxazinyl) methylenemalonate by reaction with diethylethoxymethylenamalonate. Cyclization of this malonate ester in ethylpolyphosphate gives (+,−)-ethyl 9,10-difluoro-3-methyl-7-oxo-2,3-dihydro-7H-pyrido[1,2,3-de][1,4]benzoxazine-6-carboxylate. This benzoxazine carboxylate ester is then hydrolyzed to the corresponding acid. The acid is reacted with N-methylpiperazine in dimethylsulfoxide to form Ofloxacin, 9-fluoro-10-(4-methyl-1-piperazinyl)-3-methyl-7-oxo-2,3-dihydro-7H-pyrido[1,2,3-de][1,4]benzoxazine-6-carboxylic acid. The reaction sequence is shown below:

Reaction Sequence 1

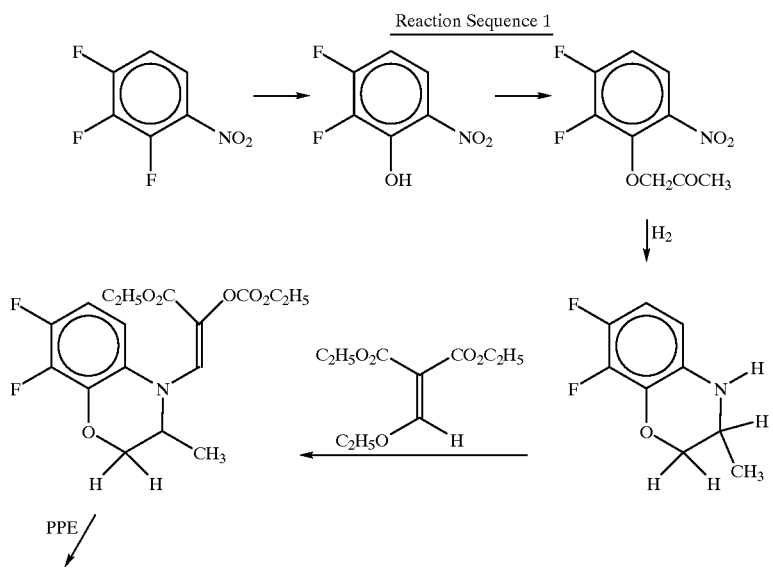

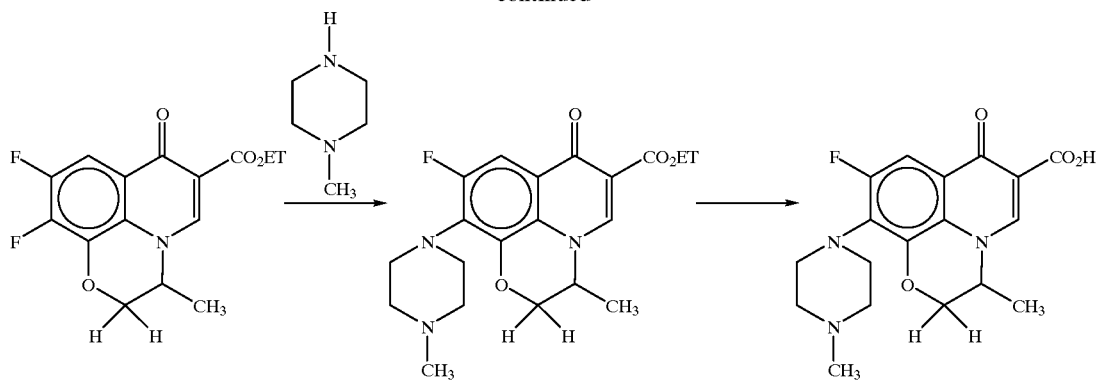

Another route to Ofloxacin is described in U.S. Pat. Nos. 4,762,831; 4,859,773; 4,958,045; and DE 3522406 A1. It utilizes tetrafluorobenzoic acid which is more expensive than intermediate trifluoronitrobenzene or the corresponding aniline. The process involves more steps than that of Hayakawa. Other routes to Ofloxacin are described in *Chem. Pharm. Bull.*, 3,4 (10): 4098–4102 (1986). This preparation is illustrated in the following reaction scheme:

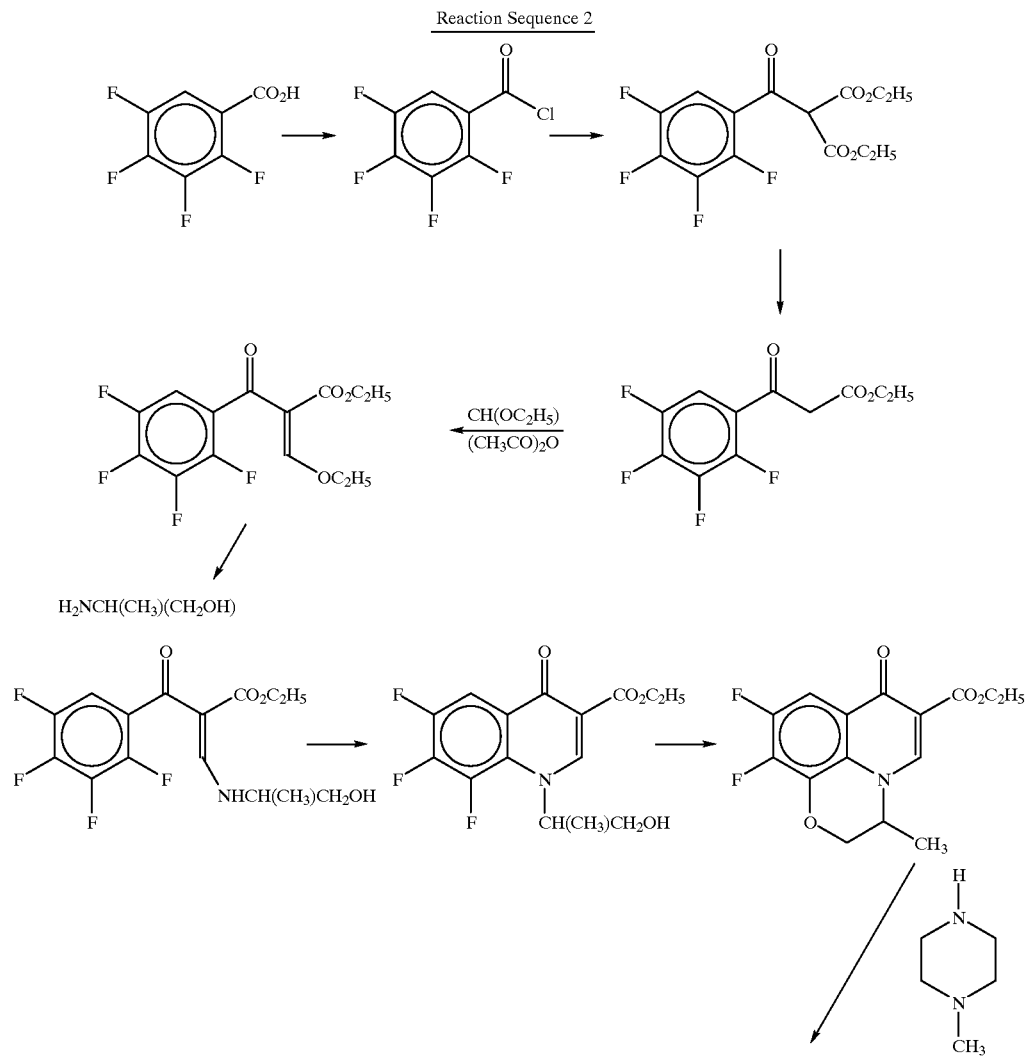

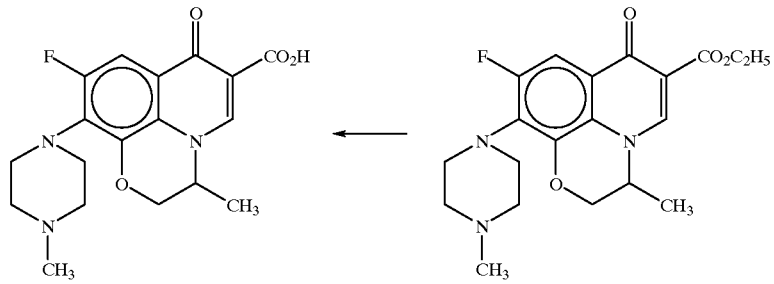

SUMMARY OF THE INVENTION

A method for the preparation of 7,8-difluoro-2,3-dihydro-3-methyl-4H-1,4-benzoxazine either as the optically active s-(−)-7,8-difluoro-2,3-dihydro-3-methyl-4H-1,4-benzoxazine or the racemic mixture. The process of the invention comprises the reaction of 2,3,4-trifluoroaniline or trifluoronitrobenzene with hydroxyacetone or a hydroxyacetone derivative under reducing condition to yield N-(3-hydroxy-2-propyl)-2,3,4-trifluoroaniline derivative. The N-(3-hydroxy-2-propyl)-2,3,4-trifluoroaniline is treated with base to yield the benzoxazine intermediate.

DESCRIPTION OF THE PREFERRED EMBODIMENTS

This invention is a simple, efficient and economical method for preparing optically active and racemic 7,8-difluoro-2,3-dihydro-3-methyl-4H-1,4-benzoxazine of the following Formula 1 in high yield under moderate conditions.

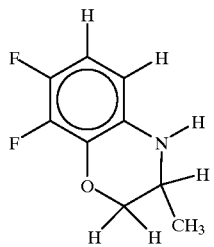

(Formula 1)

The process of this invention comprises the reaction of 2,3,4-trifluoroaniline or trifluoronitrobenzene with hydroxyacetone or a hydroxyacetone derivative such as its ester or ether under reducing conditions.

The hydroxyacetone reactant may be represented by the formula:

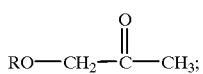

wherein

R is selected from the group consisting of H, (O)CCH$_3$, (O)CR$^1$;

R$^1$ is an alkyl group having 1 to 6 carbons, aryl such as phenyl or naphthyl, or a substituted aryl where the substituent is selected from the group consisting of C$_1$ to C$_4$ alkyl, C$_1$ to C$_4$ alkoxy, halogen, nitro, and sulfo. Hydroxyacetone is preferred.

The reducing conditions which may be used include (a) H$_2$ in the presence of a catalyst, preferably a noble metal catalyst such as platinum, palladium or ruthenium which may be optionally modified with a sulfur compound such as a sulfoxide or a nickel catalyst which may be used on a suitable support such as silica, carbon, alumina or magnesia; (b) H$_2$ in the presence of a chiral catalyst such as a chiral hydride reagent; and (c) hydrogenation with a complex metal hydride such as lithium aluminum hydride, magnesium aluminum hydride, sodium borohydride, potassium borohydride, lithium borohydride, aluminum borohydride and sodium trimethoxyborohydride. The reaction is preferably conducted under hydrogen pressure; preferably at a pressure in excess of atmospheric, for example, 3–2500 pounds per square inch (psi) and more preferably from about 400 to 1500 psi in the presence of a noble metal catalyst.

The reductive alkylation step is conducted at a temperature in excess of ambient temperature to accelerate the reaction; preferably from about 30° C. to 200° C., more preferably from about 40° C. to about 140° C. and most preferably 60° C. to 110° C. The hydrogen pressure and reaction temperature are not critical.

The reductive alkylation of an amine with an aldehyde or ketone is well known in the art; see, for example J. Amer. Chem. Soc. 60, 2023, 1938; J. Amer. Chem. Soc. 61, 3145, 1939; U.S. Pat. No. 2,298,284; Organic Preparations and Procedures Int. (4), 399–402 (1991). The reductive alkylation of an aromatic amine can be carried out on the corresponding nitro compound which is reduced to the amine and then reductively alkylated under the reaction conditions.

The reductive alkylation step may be conducted in the presence or absence of solvent or an excess of the hydroxyacetone reactant. The hydroxyacetone reactant may be used in an amount of from about 0.8 to about 4 moles per mole of the trifluoroaniline reactant. Any solvent which is inert to the reaction conditions may be used. Similarly 2,3,4-trifluoronitrobenzene may be used as a starting material and reduced to the trifluoroaniline. Suitable inert solvents include C$_1$–C$_6$ aliphatic alcohols and carboxylic acids and the esters thereof, and aromatic hydrocarbons. Exemplary solvents include acetic acid, propionic acid, methanol, ethanol, propanol, ethyl acetate, butylacetate, benzene, benzene substituted with substituted with halogen, toluene, and xylene and preferably acetic acid, methanol, ethyl acetate, butylacetate, toluene and xylene.

The catalyst for the reductive alkylation step is not critical and such catalysts are well known as described above. A preferred catalyst is a sulfided noble metal catalyst on a support. The noble metal catalysts include but are not limited to platinum, palladium, ruthenium and commonly used supports include silica, alumina, magnesia and carbon. Various additives may also be used in the reductive alkylation. Such additives include an organic acid such as acetic a buffer such as sodium acetate an amine such as a primary, secondary or tertiary amine.

A particularly preferred catalyst is a noble metal catalyst which has been sulfided on a support, such as a platinum or palladium metal which has been treated with dimethylsulfoxide on a carbon support. The most preferred catalyst is a sulfided palladium on a carbon support. Typically such supported palladium catalyst contain about 0.5 to IO percent palladium on carbon.

The reductive alkylation step can be carried in two steps first condensation of the 2,3,4-trifluoroaniline with hydroxyacetone derivative to form the imine and then reducing the imine to the amine. The reduction can be carried out utilizing a complex metal hydride such as lithium aluminum hydride, magnesium aluminum hydride, sodium borohydride, potassium borohydride, aluminum borohydride, sodium cyano borohydride, trimethoxyborohydride and chiral borohydride derivatives which can give e.e. values in the 90% range such as those discussed in M. Srebnik et al.; Aldrichimica Acta, 20,3)(1987); B. T. Cho and Y. s. Chun, Tetrahedron; Asymmetry, 3, 1583 (1992) to reduce the imine to the aminoalcohol derivative.

The reaction product of the reductive alkylation is a novel compound and has the following structure:

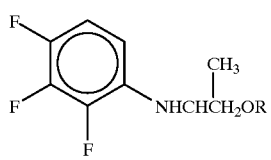

(Formula 2)

The reaction sequence for the reductive alkylation is illustrated as the following:

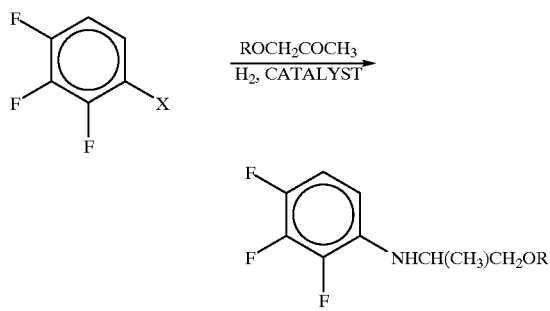

Compound of Formula 2 is treated with a base, such as an alkali metal such as sodium, potassium, lithium or an alkali metal alkoxide of a $C_1$–$C_6$ straight chain or branched alkyl such as methoxide, ethoxide, tertbutoxide; an alkali metal hydride such as sodium or potassium hydride; or an alkali metal hydroxide or carbonate such as sodium hydroxide or cesium carbonate. The ratio of base of Formula 2 to the compound can be from 1.25:1.0 to 1.0:1.0. It is preferably to use 1.0:1.0. Suitable solvent are an alcohol such as a $C_1$–$C_6$ straight chain or branched such as ethanol or tertiary butanol, or a dipolar aprotic solvent such as dimethylformamide, dimethylsulfoxide, dimethylacetamide, 1-methyl-2-pyrolidinone, hexamethylphosphorictriamide. The reaction temperature can be in a range of 40–140° C., with temperatures from 60–110° C. preferred. The reaction times can be 1–8 hours, preferably 1–4 hours to give 7,8-difluoro-2,3-dihydro-3-methyl-4H-1,4-benzoxazine, Compound of Formula 1, in high yield. The reaction sequence for the ring closure is the following:

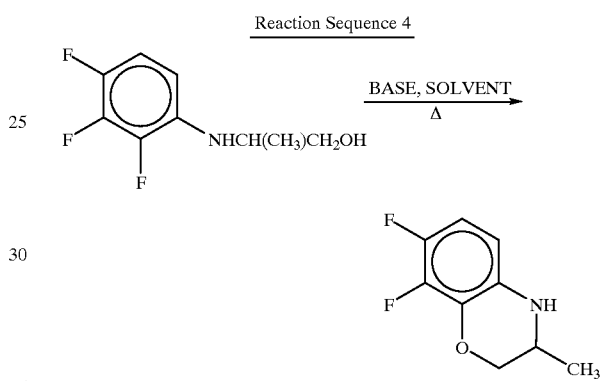

Reaction Sequence 4

The prior art method for formation of the 7,8-difluoro 2,3-dihydro-3-methyl-4H-1,4-benzoxazine is limited by the initial step of the conversion of 2,3,4-trifluoronitrobenzene to the 2-hydroxy-3,4-difluoronitrobenzene which goes in only 29% yield. This present invention results in an overall yield of 70–75% yield of the 7,8-difluoro-2,3-dihydro-3-methyl-4H-1,4-benzoxazine.

The scheme shown below illustrates the various methods the invention can be utilized with known methods to prepare the optically benzoxazine.

Reaction Sequence 5
Scheme for the Synthesis of Optically Active Intermediate

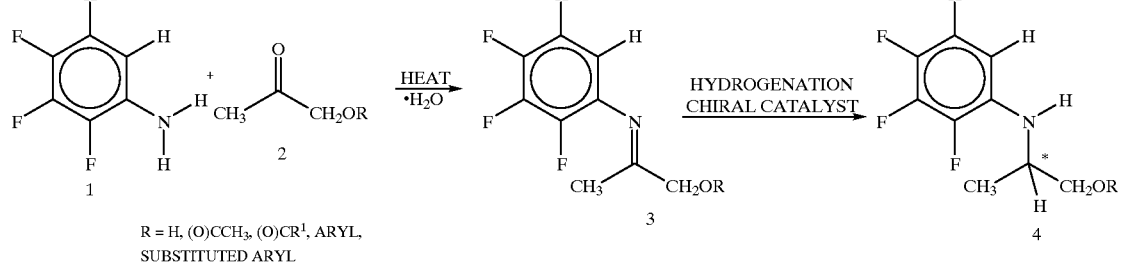

R = H, (O)CCH₃, (O)CR¹, ARYL,
SUBSTITUTED ARYL

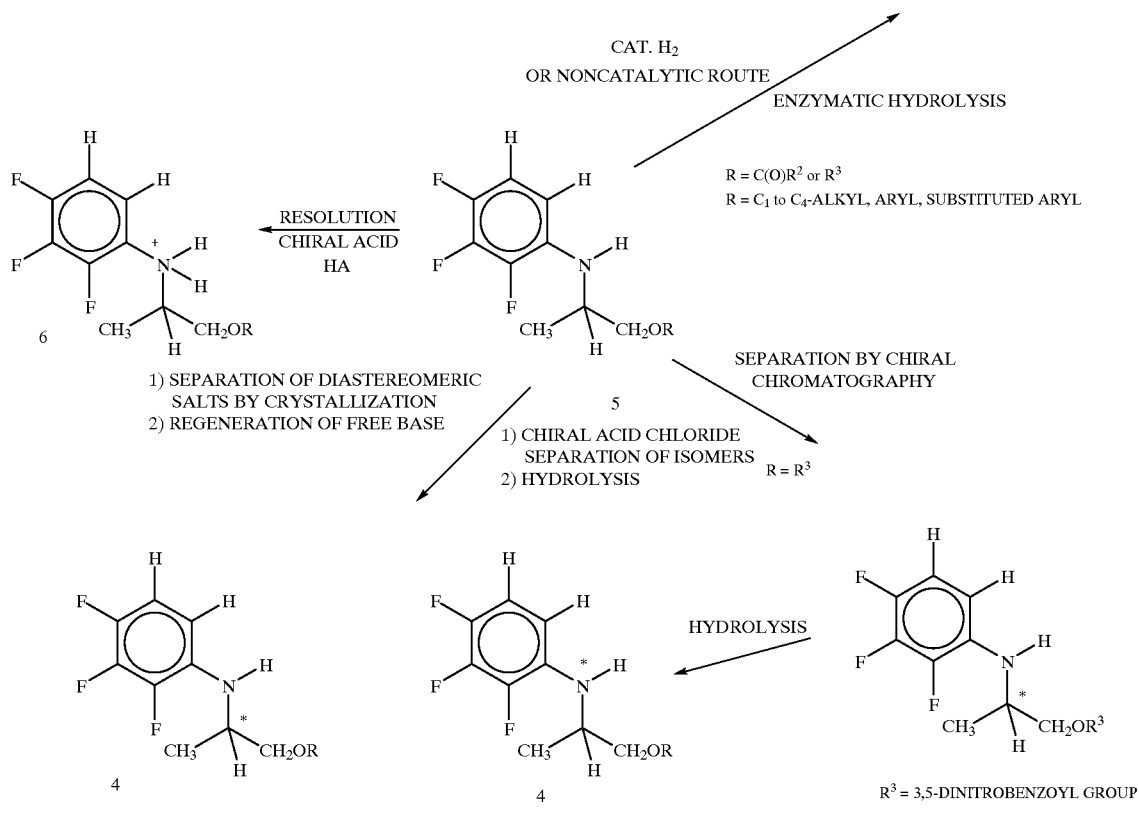

A compound of Formula 2 either optically active or inactive can be prepared from 2,3,4-trifluoroaniline or 2,3, 4-trifluoronitrobenzene and the hydroxyacetone derivative, where R is defined above, H, alkyl ($C_1$–$C_4$), (O)$CCH_1$, (O)$CR_1$ where $R_1$ is alkyl or aryl or substituted Aryl. If hydrogen and a chiral hydrogenation catalyst of platinum, palladium, optionally modified with a sulfur compound such as a sulfoxide), ruthenium, rhodium or iridium, titanium (examples of the use of these latter metals in hydrogenation chiral catalyst are given in B. Heil; *Homogeneous Catalyst with Metal Phopshine Comples*, Plenum, New York, 1983, p 335; G -J. Kang, *J. Chem. Soc. Chem. Commun.*, 1466 (1988); J. Bakos, *J. Organomet. Chem.* 370, 263 (1989); W. R. Cullen, J. Mol. Cat., 62, 1.43 (1990); H. Moser, Naturforsch., 37b, 451 (1982); A. G. Becalski, *Inorg. Chem.*, 30 5002 (1991); Y. Ng Cheong Chan, *J. Am. Chem. Soc.* 112, 9400 (1990); J. Bakos, *J. Chem. Soc. Commun.*, 1684 (1991); C. Lensink, *Tetrahedron; Assymmetry*, 3, 235 (1992); P. Kvintovics, *J. Organomet. Chem.* 361, 117 (1989); C. Lensink, *Tetrahedron; Assymmetry*, 4, 215 (1993) or a chiral hydride reagent (M. Srebnik, Aldrichimica Acta, 20, 3 (1987); B. T. Cho *Tetrahedron; Asymmetry*, 3, 1583 (1992) is utilized to reduce the Arylimine from 2,3,4-Trifluoroaniline and the Hydroxyacetone derivative the optically active aminoalcohol is obtained. The teachings of the above cited references are hereby incorporated by reference.

If non chiral reagents are used, a racemic mixture of aminoalcohols is obtained. The racemic mixture can be resolved into its enantiomers by four methods known in the literature:

1) Enzymatic hydrolysis of the mixture of racemic esters.
   Compounds of Formula 2 where R=(O)$CR_1$ where $R_1$ is the same as described above and the enzyme, can be lipoprotein lipase such as (LPL Amano 3 derived from Pseudomonas aeruginosa, produced by Amano Seiyaku K. K.) or lipase (derived from Porcine pancreas, produced by Shigma Chemical Company (U.S.A.); derived from Candida cylindracea, produced by Shigma Chemical Company; or derived from Rhizopus delemar produced by Seikagaku Kogyo Co., Ltd.
2) Chiral Chromatographic Separation of the racemic aminoalcohol derivatives. (Compounds of Formula 2 with R=3,5-nitrobenzoyl can be prepared from the racemic mixture of alcohols and 3,5-dinitrobenzoyl chloride. This mixture is separated by chiral chromatography, in a manner similar to that described in Hayakawa, I: Antimicrob. Agents and Chemother. 29; 163–164 (1986).
3) Resolution of the salts of the racemic aminoalcohol derivatives and a chiral acid by crystallization.
4) Resolution of a mixture of diasteromeric amides of the aminoalcohol derivatives followed by hydrolysis to optically pure aminoalcohol derivatives. (This can be carried out by the reaction of the aminoalcohol derivatives with a chiral acid chloride, i.e. such as an aminoacid chloride i.e. proline to give a mixture of amides which can be separated by crystallization, and upon hydrolysis of the optically pure amide, the optically active aminoalcohol derivative is obtained.)

The following examples illustrate the invention.

EXAMPLES

Example 1

Preparation of N-(3-hydroxy-2-propyl)-2,3,4-trifluoroaniline (2)

2,3,4-Trifluoroaniline was reductively alkylated in the presence of hydroxyacetone using a palladium on carbon catalyst. 30 g of a 5% Pd/C catalyst (57.3% $H_2O$)) was slurried in 200 ml of absolute methanol. The mixture was allowed to settle and 90–95% of the liquid was decanted. The process was then repeated three times. 2,3,4-trifluoroaniline (118 g, 0.8 mole) of was charged into a glass autoclave liner containing the catalyst. Hydroxyacetone (80 g, 1.08 mole) was then added and the mixture was purged with nitrogen. Hydrogenation was initiated at 65° C. and continued to a maximum temperature of 107° C. Hydrogen uptake continued for one hour at a pressure of between 430 and 450 psi at which time 75% of the alkylated product (3) was obtained with the remainder being unreacted 2,3,4-trifluoroaniline and hydroxyacetone.

Example 2

Preparation of N-(3-hydroxyl-2-propyl)-2,3,4-trifluoroaniline (2)

2,3,4-trifluoroaniline was reductively alkylated in the presence of hydroxyacetone using a sulfided palladium on carbon catalyst. 30 g of 5% Pd/C catalyst (50% $H_2O$)) was slurried in 200 ml of absolute methanol. The mixture was allowed to settle and 90–95% of the liquid was decanted. This process was repeated three times. 2,3,4-Trifluoroaniline (118 g, 0.8 mole) was charged into a glass autoclave liner containing the catalyst. Hydroxyacetone (80 g, 1.08 mole) was then added and the mixture was purged with nitrogen. Hydrogenation was initiated at 65° C. and continued to a maximum temperature of 107° C. Hydrogen uptake continued for one hour between 430 and 450 psi at which time 75% of the alkylated product (3) was obtained with the remainder being unreacted 2,3,4-trifluoroaniline and hydroxyacetone.

Example 3

Preparation of N-(3-hydroxyl-2-propyl)-2,3,4-trifluoroaniline (2)

2,3,4-trifluoroaniline was reductively alkylated in the presence hydroxyacetone using a Raney Nickel catalyst. Raney nickel (14 ml of 50% aqueous Raney nickel catalyst was slurried in 100 ml of absolute methanol. The mixture was allowed to settle and 90–95% of the liquid was decanted. The process was then repeated three times. 2,3,4-Trifluoroaniline (7.3 g, 0.05 mole) was charged into a glass autoclave liner containing the catalyst. Hydroxyacetone (3.7 g, 0.05 mole) was then added and the mixture was purged with nitrogen. Hydrogenation was initiated at 65° C. and continued to a maximum temperature of 85° C. Hydrogen uptake continued for 0.5 hour between 430 and 450 psi at which time 75% of the alkylated product (3) was obtained with the remainder being unreacted 2,3,4-trifluoroaniline and hydroxyacetone.

Example 4

Purification of N-(3-hydroxyl-2-propyl)-2,3,4-trifluoroaniline (2)

Crude N-(3-hydroxy-2-propyl)-2,3,4-trifluoroaniline (37 g, 75%) was purified via filtration of a methylene chloride solution through a bed of silica gel. The product was then removed from the silica gel with a methanol wash. The alkylation product (2) (29 g) was recovered and had a purity of 94%.

EXAMPLE 5

Preparation of 7,8-Difluoro-2,3-dihydro-3-methyl-4H-1,4-benzoxazine (1)

Purified N-(3-hydroxy-2-propyl)-2,3,4-trifluoroaniline was ring closed in the presence of a base with DMF. The trifluoroaniline intermediate (3.0 g) was diluted with 4.3 ml of DMF and added to a slurry of 0.67 g sodium hydride in 25 ml DMF at 60° C. under a positive flow of nitrogen. A temperature between 59° and 64° C. was maintained. The reaction flask was heated at 60° C. for an additional 4 hours and then allowed to cool to room temperature. Excess sodium hydride was with glacial acetic acid which left the mixture at a pH of approximately 8. A major portion of the DMF was distilled off under reduced pressure. The concentrated solution was then transferred to a separatory funnel where the salts were extracted from the methylene chloride layer using deionized water. The organic layer was dried with magnesium sulfate, filtered and evaporated to yield 2.6 g (96%) of the dark brown liquid (1).

Analysis

All analysis was done on a Hewlett-Packard 5890 gas chromatograph.

Example 6

Reaction was run similar to Example 5 wherein the base was sodium methoxide and the temperature was 65° C. 61% of the benzoxazine product was generated.

Example 7

Reaction was run similar to Example 5 wherein the base was potassium tert-butoxide and the temperature were 90–120° C. 16–40% of 7,8-Difluoro-2,3-dihydro-3-methyl-4H-1,4-benzoxazine was generated.

Example 8

Reaction was run similar to Example 5 wherein the was cesium carbonate. The reaction temperature was 105° C. 50% of the desired product was generated.

Example 9

Reaction was run similar to Example 5 wherein sodium hydroxide was utilized as the base and the temperature was 105° C. 29% of 7,8-Difluoro-2,3-dihydro-3-methyl-4H-1,4-benzoxazine was generated.

Example 10

Reaction was run similar to Example 5 wherein the heating time was 1 hour. The conversion was 100%.

Example 11

Reaction was run similar to Example 5 the ratio of starting material to NaH base was 1:1. 63% of the desired product was generated.

Example 12

Reaction was run similar to Example 5 wherein the ratio of N-(3-hydroxy-2-propyl)-2,3,4-trifluoroaniline to sodium hydride was 1:1.5. 100% of 7,8-difluoro-2,3-dihydro-3-methyl-41H-1,4-benzoxazine was generated.

Example 13

Reaction was run similar to Example wherein the sodium hydride was slurried in 5 g of DMF. 7,8-difluoro-2,3-dihydro-3-methyl-4H-1,4-benzoxazine was generated in 76% of theory.

Example 14

Reaction was run similar to Example 5 wherein the sodium hydride was slurried in 1 g of DMF. 7,8-difluoro- 2,3-dihydro-3-methyl-4H-1,4-benzoxazine was generated in 64% of theory.

Example 15

Reaction was run similar to Example 5 wherein the solvent used was DMSO, 100% of the desired product was generated.

The following description is given to illustrate the invention and is not intended to limit the invention or the claims hereof. Various modifications of the description and the claims will be obvious to one of ordinary skill in the art and such obvious modifications are within the invention. The term, hydroxyacetone reactant is intended to mean hydroxyacetone and its ester and ether derivatives as defined herein. Similarly the term, N-(3-hydroxy-2-propyl)-2,3,4 trifluoroaniline or derivative thereof is intended to mean said trifluoroaniline and the corresponding esters and ethers thereof within the scope of the definition of the substituent R previously defined herein.

I claim:
1. A compound of the formula:

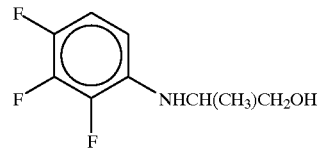

* * * * *